United States Patent [19]

Boucher

[11] 3,968,250

[45] *July 6, 1976

[54] METHOD AND SPORICIDAL COMPOSITIONS FOR SYNERGISTIC DISINFECTION OR STERILIZATION

[75] Inventor: Raymond Marcel Gut Boucher, New York, N.Y.

[73] Assignee: Wave Energy Systems, Inc., New York, N.Y.

[ * ] Notice: The portion of the term of this patent subsequent to June 25, 1991, has been disclaimed.

[22] Filed: July 16, 1975

[21] Appl. No.: 596,289

Related U.S. Application Data

[63] Continuation-in-part of Ser. No. 486,210, July 5, 1974, abandoned, which is a continuation-in-part of Ser. No. 155,233, June 21, 1971, abandoned.

[52] U.S. Cl. .................................................. 424/333
[51] Int. Cl.² .......................................... A01N 9/24
[58] Field of Search ....................................... 424/333

[56] References Cited
UNITED STATES PATENTS

| | | | |
|---|---|---|---|
| 2,801,216 | 7/1957 | Yoder et al. | 424/333 |
| 3,016,328 | 1/1962 | Pepper et al. | 424/333 |
| 3,057,775 | 10/1962 | Rendon | 424/333 |
| 3,282,775 | 11/1966 | Stonehill | 424/333 |
| 3,497,590 | 2/1970 | Elgin | 424/55 |
| 3,503,885 | 3/1970 | Wedell | 252/95 |
| 3,650,964 | 3/1972 | Sedilar | 252/106 |
| 3,666,668 | 5/1972 | Klausner | 424/329 |
| 3,697,222 | 10/1972 | Sierra | 21/58 |

FOREIGN PATENTS OR APPLICATIONS

| | | | |
|---|---|---|---|
| 865,913 | 3/1971 | Canada | 21/7 |

OTHER PUBLICATIONS

"Potentially Infectious Agents . . . Aeruginosa," Wilkoff et al., Applied Microbiology, Apr. 1971, pp. 647–652.
"Potentially Infectious . . . Bed Pans," Sidewell et al., 19(1)53–59(1970).
"Preservation of Toilet . . . Nonionics", Wedderburn, et al., J. of Soc. Cos. Chemists, 210–228 (1958) (11–29–1957).
J. of Pharm. Science 53 (10) pp. 1273–1275 (1964). Berick et al., — "Alkalinized Glutaraldehyde . . . Agent".
Currents in Mod. Biology 1, pp. 14–20, (1967), Egyrid – "Studies on Cell Division".

Primary Examiner—Albert T. Meyers
Assistant Examiner—D. W. Robinson
Attorney, Agent, or Firm—Shoemaker and Mattare, Ltd.

[57] ABSTRACT

This invention relates to a method for disinfecting or sterilizing medical, surgical, dental instruments or other objects in liquid phase with improved sporicidal compositions. The method object of the invention is based upon the synergistic effects observed when combining non-ionic and anionic surfactants with aqueous or alcoholic glutaraldehyde solutions. The method can be used also with ultrasonic irradiation over a wide frequency range (10 to 850 kHz). Two types of particularly effective synergistic sporicidal compositions are also described. Another modification is the use of the composition for disinfecting broiler eggs in breeder farms and commercial hatcheries.

5 Claims, No Drawings

METHOD AND SPORICIDAL COMPOSITIONS FOR SYNERGISTIC DISINFECTION OR STERILIZATION

CROSS REFERENCE TO RELATED APPLICATION

This application is a continuation-in-part application of copending application Ser. No. 486,210, filed July 5, 1974, entitled "Method and Sporicidal Compositions for Synergistic Disinfection or Sterilization", which in turn is a continuation-in-part application of Ser. No. 155,233, filed June 21, 1971, entitled "Method and Sporicidal Compositions for Synergistic Disinfection or Sterilization" both now abandoned.

BACKGROUND OF THE INVENTION

This invention relates to a method for disinfecting or sterilizing objects in liquid phase with improved chemosterilizer compositions. The method object of our invention is based upon the synergistic sporicidal effects observed when using relatively moderate temperatures combined or not combined with ultrasonic irradiation in specially formulated sporicidal compositions. The latter are based upon active combinations of glutaraldehyde with nonionic surfactants such as ethoxylates or isomeric linear alcohols ($C_{11}$ to $C_{15}$) or anionic alkyl aryl sulfonates.

Through a proper choice of temperatures, acoustic energy density and chemical composition, the method object of the present invention enables reducing from hours to minutes the time requirements for surface disinfection or sterilization of heat sensitive materials.

Low temperature surface sterilization in liquid phase has been limited in the past to the use of two chemosterilizer agents: formaldehyde and alkaline glutaraldehyde solutions. This limited choice indeed contrasts with the large number of chemical bactericides available (Quarternary Ammonium compounds, chlorine containing compounds, Iodophores, Amphoteric compounds, etc.) when one does not require sporicidal action.

Formaldehyde is one of the oldest chemosterilizers employed for the destruction of spores, and, although 1 to 2% solutions have been used, a relatively long period of time (up to 20 hours) is required to destroy *Bacillus subtilis* var. niger spores. A somewhat shorter time is needed if one uses higher concentrations of formaldehyde (around 8 per cent) in isopropyl alcohol. This solution, called Formalin has several drawbacks. The irritating fumes of formaldehyde limit its usefulness, and its toxicity for tissue requires that disinfected materials be thoroughly rinsed with sterile water before use.

Alkalinized glutaraldeyde solutions known commercially under the trade name CIDEX are the only widely used for practical applications today. They consist of 2% aqueous glutaraldehyde solution buffered by suitable alkalinating agents (generally 0.3% sodium bicarbonate) to pH of 7.5 to 8.5. In the acid state at room temperature the glutaraldehyde solution is stable for long periods of time when stored in a closed container. However, when rendered alkaline, the glutaraldehyde gradually undergoes polymerization and loses its activity. Above pH 9 the polymerization proceeds very rapidly. In the 7.5 to 8.5 pH range polymerization is slower, but it is acknowledged by the manufacturer himself that sporicidal activity disappears after two weeks. (ARBROOK, Bulletin JR 8016, 1968)

Even when using a fresh solution of 2% buffered glutaraldehyde, the time needed at room temperature to achieve complete sterilization of *Bacillus subtilis* with the AOAC Pennycylinder method is said to be comprised between 3 and 10 hours according to spore dryness.

The impossibility to store the sporicidal solution over extended periods of time, the need to buffer each time before use and the long contact time required (several hours) to achieve sterility made us develop the method and new sporicidal composition objects of the present invention.

As hereabove stated, Alkalinized Glutaraldehyde has been widely used as a chemical sterilizing agent since its antimicrobial characteristics were first described in the U.S. Pat. No. 3,016,328 (1962). R. E. Pepper and E. R. Lieberman were the first to point out in the abovementioned patent that aqueous glutaraldehyde solutions were mildly acid and in this state they stressed that they did not exhibit sporicidal characteristics. Only when the solution was buffered by suitable alkalinating agents to a pH of 7.5 to 8.5, did the solution become antimicrobially active. (see American Journal of Hospital Pharmacy 20: 458–465, Sept. 1963) This point was emphasized in the U.S. Pat. No. 3,016,328 (1962) which stated (page 1, column 2, line 34) that the invention resided in the discovery that a saturated dialdehyde containing 2 to 6 carbons does, in fact, have sporicidal activity when it is combined with a lower alkanol and an alkalinating agent.

More recently G. Sierra in Canada (Can. Patent No. 865,913, March 1971) showed that the conclusions of R. E. Pepper and E. R. Lieberman were only valid in the temperature range (22°–23°C) indicated by these authors in their U.S. patent. The Sierra's Canadian patent indicates that strong sporicidal activity is exhibited by acid non-buffered non-alkalinized glutaraldehyde solutions when operating at temperatures higher (generally around 45°C) than those mentioned in R. E. Pepper's patent. This observation was confirmed in our own experiments. Moreover, we found, and this is one of the objects of the present invention, that with the proper combination of acid glutaraldehyde with certain nonionic or anionic surfactants at temperatures greater than 15°C but specially above 45°C higher sporicidal activities than those mentioned in G. Sierra's patent can be achieved.

An increase in bactericidal and sporicidal activity through the combined use of glutaraldehyde (both acid and alkaline) with surfactants had been previously disclosed by A. A. Stonehill in U.S. Pat. No. 3,282,775 (Nov. 1966). This inventor, however, referred only to the use of cationic agents. Several examples were given in the A. A. Stonehill patent. They all pertained to chemical compositions using glutaraldehyde solutions with quaternary ammonium salts or cetylpyridinum chloride both of which exhibited sporicidal characteristics at room temperature within the 4 to 9 pH range.

It is an object of the present invention to show that a glutaraldehyde solution combined with nonionic or anionic agents such as ethoxylates of isomeric linear alcohols or alkyl aryl sulfonates is far more active than any other previously known sporicidal formula based upon the mixing of glutaraldehyde with cationic agents.

It is a further object of the present invention to show that the combined use of glutaraldehyde solutions with nonionic or anionic surfactants is effective over a wider pH range (1 to 9) while also working at any temperature inside the 15° to 75°C range.

It is a further object of this invention to show that one can considerably reduce the sterilization time through simultaneous sonic or ultrasonic irradiation of the sporicidal compositions based upon a mixture of glutaraldehyde with nonionic or anionic surfactants.

To aid in the understanding of our invention, we shall briefly review the various physical or chemical mechanisms which play a role in the strong sporicidal effects observed in the method object of the present invention.

A few bacteria have evolved a highly effective mechanism for ensuring their survival; they exhibit an elementary form of differentiation in which, under certain conditions, the relatively sensitive vegetative form of the organism can give rise to a resistant dormant form, called a spore. Bacterial spores are much more resistant to adverse effects of heat, radiation and chemicals than their corresponding vegetative cells. The resistance of spores differs within the microbial population and species variation is common. Among the spores which were used to evaluate the methods object of the present invention, we shall mention *Bacillus subtilis*, *Bacillus stearothermopilus*, *Bacillus pumilus*, *Clostridium sporogenes*, and *Clostridium tetani*.

A bacterial spore is typically about one micro diameter and consists essentially of a small cell, often called the core of spore protoplast, surrounded by a number of specialized layers. The principal layers are the thick cortex and the multilayered coats and, around spores of certain species, a further loose and thin layer called exosporium.

At the moment it is believed (C. S. Phillips, Bact. Rev. 1962) that alkylating agents such as ethylene oxide, β propiolactone, formaldehyde, glutaraldehyde as well as other aldehydes attack the sulfhydryl (—SH), hydroxyl (—OH), amino (—NH$_2$) and carboxy

groups present in spore cell proteins. More recently T. J. Munton and A. D. Russell (J. Appl. Bact., 1970) stated that the chemical sites for glutaraldehyde action could involve —NH$_2$ groups, including cross linking reactions between these groups (D. Hopwood, Histochemie, 1968). According to these authors, however, the suggested mechanism does not exclude sites of action with other chemical groups.

T. J. Munton and A. D. Russell (J. Appl. Bact. 1970) also showed that the uptake of acid glutaraldehyde and alkaline glutaraldehyde (sodium bicarbonate buffer) is similar and that both are of the Langmuirian type. This was demonstrated with E. Coli and Bacillus megatorium. In other words as more sites of the bacterial cell or spores are filled, glutaraldehyde molecules find increasing difficulty in attaching themselves to the cell or spore. In the methods object of the present invention it is believed that the nonionic linear alcohol ethoxylates decrease the surface tension and increase the wettability at the spore/liquid interface in such a manner that they promote a faster absorption rate of glutaraldehyde molecules. This could also be the result of the entrapping at the spore/liquid interface of a higher concentration of glutaraldehyde molecules, said phenomenon being increased in a logarithmic manner with temperature inside the 15°–75° range. Although of a lower magnitude, the same increased rate of absorption at the spore/liquid interface is observed with anionic alkyl aryl sulfonates mixed with nonionic polyoxyethylene alcohol ethers.

When speaking of absorption rates, one must point out that the increased wettability observed with the sporicidal molecules could be due not only to an increase at the external spore interface but also to a faster penetration inside the internal spore interfaces, i.e., across cortex layers, cortex or plasma membrane.

If using one of the sporicidal compositions object of the present invention in combination with ultrasonic irradiation extremely high killing rates are observed. This indeed could be explained in the following manner. As well known, the major component of a spore cortex layer is a polymer called murein (or peptidoglycan). Murein is present in lesser amounts in the walls of all bacteria. It is a large, cross-linked, net-like molecule exhibiting several unusual features. This polymer is acidic, and in spores may exist as a layer tightly contracted by some positively charged molecules. One recent theory to account for the extreme heat resistance of spores supposes that contractile pressure exerted by this structure may squeeze the central core sufficiently to maintain it in a state so dry as to confer heat resistance. Ultrasonic irradiation is one of the most efficient techniques (KY Sergeeva, Sov. Phys. Acoust., March 1966) to shake up polymer lattices and produce a fast depolymerization. This technique is said to be quite efficient over a wide frequency range both at low (G. Schmid et al., Kolloid L, 1951) and high frequency (M. A. K. Mostafa, J. Polym. Sci. 1958). it is, therefore, understandable that murein depolymerization or a partial destruction of the tight cross-linked lattice would enable the aldehyde groups to penetrate and combine faster with the active spore sites. Nonionic and anionic surfactants will indeed accelerate the penetration through the loosened polymer lattice. High intensity ultrasonic energy could also play an important role through other secondary but important mechanisms.

The proteinaceous outer coats of spores contain a disulfide-rich protein with some properties close to those of keratins. Since keratin-like proteins are typically strong, inert towards chemical reagents and resistant to enzymes they constitute an ideal protective barrier for spores. High intensity ultrasonics, however, could physically degrade keratin (J. H. Bradbury, Nature, 1960) and thus promote a faster penetration of active glutaraldehyde molecules.

Two more components characteristic of spores are high levels of calcium (often two percent of the spore's dry weight) and dipicolinic acid (DPA) which may account for over 10 percent of a spore's dry weight. Under acoustic turbulence ions exchange (Ca depletion) can take place while the heterocyclin DPA molecule could also be broken (I. E. Elpiner and A. V. Sokolskaya, Sov. Phys. Acoust. March 1963). In short, ultrasonic energy could either accelerate the physical diffusion of molecules or active radicals to reaction sites inside the spores, produce chemical bonds breakages of critical spores components (including sites modification) or both. It could also, specially with alkaline glutaraldehyde, depolymerize some of the glutaraldehyde in solution. This could be of particular significance when one remembers that alkalinized glutaraldehyde gradually loses its activity when polymerization progresses. (A. A. Stonehill et al, Am. Journ. Hosp. Phar. 1963).

Although the synergistic sporicidal effect due to a combination of moderate heat, glutaraldehyde solution and high intensity ultrasonics has been described already in G. Sierra's patent (Canadian Patent Application, No. 098,416, 1971), the present invention shows that an addition of nonionic or anionic surfactants to the glutaraldehyde solution leads in all cases to a substantial increase in bacteria, virus, or spore killing rate.

Having described our sterilization method and the sporicidal compositions to be used with it, we shall now give several examples to further illustrate the invention. They are given primarily for the purposes of illustration and should not be construed as limiting the invention to the details given.

EXAMPLES

A novel aqueous bactericidal, virucidal and sporicidal composition of the present invention is prepared with 2 percent glutaraldehyde (Union Carbide grade) and 0.2% of a nonionic surface active agent (TERGITOL 15-S-12) made by Union Carbide which is a mixture of ethoxylates of isomeric linear alcohols. The linear alkyl hydrophobic portion of the surfactant being a mixture of $C_{11}$ to $C_{15}$ linear chains. The hydrophylic portion being a polyoxyethylene chain (9 to 13 oxyethylene groups) randomly attached to the linear aliphatic chain through an ether linkage as shown in the following formula:

$$CH_3-(CH_2)_n-CH_3 \quad 9<n<13.$$
$$O-(CH_2-CH_2O)_x-H \quad 9<x<13$$

The nonionic surfactant used in the formulation object of the present invention (TERGITOL 15-S-12) made by Union Carbide had the following characteristics: Molecular weight 728, Cloud point (1% aqueous solution) 90°C, Pour point 17°C, 100% solubility in water at 25°C, Apparent specific gravity 20/20°C: 1.023, density 8.49 lb/gal at 30°C, viscosity 48 CKS at 40°C, flash point 460°F. (ASTM method D 92).

The anionic surfactant blend with nonionic polyoxyethylene alcohol ethers used in the second formulation object of the present invention had the following characteristics: Specific gravity 1.02, density 8.5 lb/gal, clear liquid soluble in hot or cold water, pH comprised between 6 and 8, freezing point −10°C.

The Union Carbide grade of glutaraldehyde concentrate which was used to prepare the 2% solution used in our tests had the following characteristics: Specific gravity 1.058 to 1.065 at 20°C, glutaraldehyde concentration 24.5 t0 25.5 percent by weight, pH 2.7 to 3.7 at 25°C, Acidity 0.2 percent by weight, maximum, calculated as acetic acid, iron content less than 3 ppm, heavy metals content less than 2 ppm, color 125 platinum-cobalt maximum.

The spores against which the solutions have been tested were vacuum dried strains of Clostridium Sporogenes (ATCC 7955), *Bacillus globigii*, *Bacillus pumilus*, *Bacillus stearothermophilus* and *Bacillus substilis*.

The latter showed the great resistance to the sporicidal composition and for the sake of clarity, we shall restrict ourselves to the presentation of data pertaining to this microorganism.

Tests were conducted in specially designed ultrasonic stainless steel tanks (Wave Energy Systems series CTG 160) with a 2 gallon capacity. The acoustic output in liquid phase could vary from 10 to 30 watts per liter of spores suspension. The experimental irradiation frequency was either 10 kHz or 27 kHz (± 1 kHz). At high frequency (850 kHz, 20 watts/liter and 5 watts/cc) the spore solution was contained in a 2 gal glass beaker which was placed in a water filled container fitted at the bottom with a submersible transducer (glazed cobalt lead zirconate titanate). During all experiments the temperature was thermostatically controlled at ± 1°C.

As previously stated, spores of *Bacillus subtilis* (ATCC 6051) were used in all the reported experiments. The preparation of clean spores was accomplished with the G. Sierra and A. Bowman technique (Journ. Appl. Microbiology, 17: 372–378, 1969). The spores were pasteurized (80°C, 15 min.) and stored at 4°C as concentrated suspensions in deionized water and used within 1 week. The standardization of the spore suspensions was carried out as described by G. Sierra (Can. Journ. Microbiology, 13: 489–501, 1967).

Glutaraldehyde and glutaraldehyde/surfactant solutions were freshly prepared in deionized water for each experiment. Concentrated stock solution of the buffers or sodium bicarbonate were added separately to pasteurized spore suspensions. The pH values reported here are those of a complete system after all additions and were read with a Beckman Zeromatic II pH meter, the calibration of which was checked before each assay was run. Stirring was continuous, and the pH was read after allowing the electrode potential to stabilize.

To recover spore survivors efficiently (especially in the lower dilutions) the effects of glutaraldehyde carryover into the viable count plates was counteracted by quenching the glutaraldehyde with sodium bisulphite before plating. After the desired treatment samples of 0.5 ml were taken to determine the numbers of surviving spores. Each sample was diluted immediately into 4.5 ml of 1% sodium bisulphite + 0.1% peptone solution and allowed to stand for 10 minutes, after which further serial dilutions were made in 0.5% sodium bisulphite + 0.1% peptone solution. Colony counts from 0.1 ml amounts of appropriate dilutions were made on 0.1% starch-nutrient agar; duplicate plates were incubated at 30°C for 3 days. The bisulphite treatment was found neither to potentiate glutaraldehyde induced spore inactivation nor cause detectable direct inactivation of intact spores.

In a few instances it could be of interest to use as a diluent not only filtered deionized water but a lower alkanol such as methanol, ethanol, isopropanol and the like. A mixture of both could also be used and in Table IV, we give the results of a test conducted with a composition comprising 60% isopropyl alcohol with 37.8% water, 2% glutaraldehyde and 0.2% nonionic surfactant. Tables 1 to V show some typical results of our experiments conducted with suspensions of *Bacillus subtilis* (ATCC 6051) under variable conditions (glutaraldehyde concentration, different surfactants, varying temperature and pH).

TABLE I

Various concentration of glutaraldehyde
Initial spores count $10^7$/ml. temperature 55°C.
Ultrasonic field: Frequency 27 kHz, Intensity 20 watts/liter pH5.

| Glutaraldehyde Concentration | Minimum time in minutes for 100% kill |
|---|---|
| 0.1% | 20 with ultrasound |
| 2 | 15 with ultrasound |
| 5 | 15 with ultrasound |

TABLE I-continued

Various concentration of glutaraldehyde
Initial spores count 10⁷/ml. temperature 55°C.
Ultrasonic field: Frequency 27 kHz, Intensity 20 watts/liter pH5.

| Glutaraldehyde Concentration | Minimum time in minutes for 100% kill |
|---|---|
| 0.1 | 40 no ultrasound |
| 2 | 30 no ultrasound |
| 5 | 30 no ultrasound |
| 2 | 10 with ultrasound and nonionic surfactant (0.2%) |
| 2 | 20 no ultrasound but with nonionic surfactant (0.2%) |

TABLE II

Various concentration of different synergistic surfactants
Initial spores count 10⁷/ml temperature 55°C
Ultrasonic field: Frequency 27 kHz, Intensity 20 watts/liter
Glutaraldehyde concentration: 2%

| Type of surfactant | Surfactant concentration | Minimum time in min. for 100% kill |
|---|---|---|
| nonionic* | 0.2% | 11 |
| nonionic | 0.2 | 10 |
| nonionic | 1 | 10 |
| anionic** | 0.02 | 12 |
| anionic | 0.2 | 11 |
| anionic | 1 | 11 |
| cationic*** | 0.2 | 15 |
| no surfactant (glutaraldehyde alone) | | 15 |

\* ethoxylates of isomeric linear alcohols
\*\* alkyl aryl sulfonate mixed with polyoxethylene alcohol ethers
\*\*\* cetylpyridinium chloride

TABLE III

Activity at various temperatures
Initial spores count 10⁷/ml
Ultrasonic field: Frequency 27 kHz, Intensity 20 watts/liter Glutaraldehyde concentration 2% - Nonionic surfactant concentration: 0.2% pH 5

| Temperature | Minimum time in min. for 100% kill |
|---|---|
| 15°C | 120 |
| 25°C | 100 |
| 45°C | 60 |
| 55°C | 10 |
| 65°C | 5 |

TABLE IV

Activity at various pH 5
Initial spores count 10⁷/ml
Ultrasonic field: Frequency 27 kHz, Intensity 20 watts/liter Glutaraldehyde concentration 2%, Nonionic surfactant concentration: 0.2% Temperature: 55°C

| Diluent | pH | Minimum time in min. for 100% kill |
|---|---|---|
| Deionized water | 2.5 | 11 |
| Deionized water | 5 | 10 |
| Deionized water | 6 (with buffer) | 10 |
| Deionized water | 8 (with buffer) | 10 |
| Deionized water | 10 (with buffer) | 12 |
| Water and isopropyl alcohol (66%) | 6.5 | 10 |

TABLE V

Activity at various ultrasonic frequencies and intensities
Initial spores count 10⁷/ml.
Glutaraldehyde concentration 2%, nonionic or anionic surfactant concentration: 0.2% Temperature: 55°C pH 6

| Type of Surfactant | Ultrasonic Frequency in kHz | Energy density | Minimum time in min. for 100% kill |
|---|---|---|---|
| nonionic | 27 | 20 watts/liter | 10 |
| nonionic | 27 | 30 watts/liter | 6 |
| nonionic | 27 | 1 watt/liter | 18 |
| nonionic | 10 | 20 watts/liter | 10 |
| nonionic | 10 | 30 watts/liter | 6 |
| nonionic | 850 | 20 watts/liter | 12 |
| nonionic | 650 | 5 watts/cc | 4 |
| anionic | 27 | 20 watts/liter | 12 |

The data contained in these tables clearly show the synergistic effects obtained with two types of sporicidal compositions based upon nonionic and anionic surfactants dissolved in glutaraldehyde. They also show that the teachings of the invention may be practiced within the following parameters:

Glutaraldehyde concentration: from about 0.1% to 5%.

Nonionic, or anionic blend with nonionic surfactant: from about 0.1% to about 1%.

Acoustic field frequency: from about 10kHz to about 850kHz.

Acoustic field energy density: from about 1 watt/liter to about 5 watt/cc

Diluent: water or lower alkanol

Temperature: above 15°C pH range: 2 to 10

Another successful application of the composition of the invention is the processing of broiler eggs in breeder farms and commercial hatcheries. It is well known that the broilers industry had always an important proportion of losses during the various stages of its complex operation (from eggs collection to chicken raising).

One of the most important causes for broiler eggs infertility and losses has been microbiological contamination. The average overall infertility and losses for broiler eggs in a standard commercial operation could vary between 10 to 20% according to the type of processing plant, the method of collection at the breeder farm, the temperature and numerous other variables.

The major cause of failure in the hatching process is due to bacteria growth on the egg surface and this indeed leads to subsequent microorganism penetration through the shell. This results in eggs that fail to hatch and are known in the industry as "poppers" or exploders. The so called poppers are eggs that literally explode due to bacteria action and spew their content (with its contamination) over adjacent eggs and sometimes over the entire tray. This does not only contaminate other eggs in the vicinity but makes subsequent cleaning and sanitation of the trays very difficult.

To alleviate this problem, eggs processing necessitates both a thorough washing step to eliminate soil, animal fecis, organic matter and a disinfection or sanitizing step. The washing step is accomplished batchwise or in a continuous manner by submitting the eggs to a detergent spray or dipping them in a surfactant non toxic solution. The disinfecting or sanitizing stage consists of fumigating of eggs dipping in a bactericidal solution containing products such as formaldehyde, iodophores, phenols, mercury salts or quaternary ammonium compounds. It has been found that the composition of the invention can be successfully used to achieve in one step both the cleaning and disinfecting of eggs. The presence of the nonionic ethoxylates of isomeric linear alcohols provides strong detergency characteristics to the solution which also exhibits a high level of cidal efficiency against vegetative organisms, viruses, mycobacteria, salmonella, pseudomonas, fungi and wet bacterial spores.

The relative cleanliness of the processed eggs varies according to the breeder farms. In some farms the hens lay on the floor of the breeder house rather than placing their eggs in the nest. Such floor eggs are usually highly contaminated since they rest and cool in the litter rather than in the much cleaner environment of the nest. Duck and turkey eggs are collected faster in some modern high volume hatcheries and therefore go to processing in a cleaner state with less organic matter and a lower microorganisms content. The results of the treatment with the disinfecting solution of the present invention will greatly vary according to the initial degree of contamination of the fowls' eggs.

Table VI shows an 8% gain in hatchability when dipping fertile broiler eggs in an aqueous solution containing 2% of glutaraldehyde and 0.25% of nonionic ethoxylates of isomeric linear alcohols. Each treatment consisted of 24 eggs. Eggs were set and hatched with regular production tray.

Table VII gives cidal data pertaining to the above described test. Each of five eggs selected at random from each treatment were swabbed using one CALGITUBE (Colab Laboratories) moistened with 0.85% saline. One square inch of surface was swabbed by using 10 vertical strokes and 10 horizontal strokes while turning the swab. Swabs were dissolved in 4 ml of 1% sodium citrate and known dilutions plated out.

From Table VII one can see that only untreated eggs had viable microorganisms. Pooled samples from each treatment were tested for Salmonella. None were detected. Eggs were exceptionally clean and the small number of bacteria isolated could be explained by this factor.

Following this study comparative tests were conducted in a hatchery by dipping the eggs during 30 seconds in an aqueous 2% solution of glutaraldehyde with 0.25% of nonionic ethoxylates of isomeric linear alcohols as a biocidal synergistic additive.

The results are given in Table VIII and they show an average boost of 7.5% in hatchability when comparing the normal process with the potentiated glutaraldehyde 30 seconds dipping. It is also of interest to recall that another series of tests with glutaraldehyde alone (no potentiating nonionic additive) showed only an insignificant 1% yield increase.

To clearly show the differences in hatchability gain according to the cleanliness of the processed eggs other tests were conducted in the laboratory with the nest clean eggs, nest dirty eggs, and floor eggs. The results are given in Table IX. They show that while an increase in hatchability of the order of 5% can be expected with nest eggs, a far more substantial increase (nearly 30%) is observed when handling the highly contaminated floor eggs.

A subsequent series of tests conducted under identical experimental conditions showed that the same results could be obtained with an aqueous glutaraldehyde solution containing 1% of active ingredient and 0.125% of nonionic additive as can be seen in Table X. No significant difference was found in hatchability gain when using a 12 months old solution which has been previously used for various disinfecting operations of heavily contaminated trays and instruments.

Other experiments conducted with a large number of clean duck eggs (around 40,000 eggs set) has shown that one can expect an increase in hatchability of 3 to 5% when comparing the 1% potentiated glutaraldehyde to a non-treated lot. The yield increase in this case is comparable to the one observed with the standard chlorination method but using the composition of the invention enables the recycling of the disinfectant solution thus providing an important economic advantage.

Another field study was conducted with turkey eggs comparing a 2% potentiated glutaraldehyde solution with an iodine-detergent sanitizer. Eggs from 2 pens of 1,000 birds each were saved for test periods of one day each at two week intervals. Eggs were hand cleaned with sand paper and placed in wire baskets for dipping. Eggs from pen 1 were dipped for 30 seconds in a 2% potentiated glutaraldehyde solution. After dippings the eggs were allowed to dry, then placed on clean filter flats and incubated three days later. A 20 egg sample from each treatment plus 5 untreated eggs (controls) were individually plated on a Rodak plate for gross bacterial counts. Swabs were taken to test for presence of Salmonella and Proteus. All eggs were hatched in the same incubator.

Eggs dipped in potentiated glutaraldehyde had significantly lower bacteria counts than eggs dipped in the iodine-detergent and non-dipped controls. The average colony count per plate was 23, 74 and 774, respectively. Salmonella was not observed in any cultures.

This test showed that the high cidal efficacy of the composition of this invention will provide an enormous margin of safety during periods when a heavy microbiological contamination occurs for various known or unknown reasons. Contrary to phenols, the formulation of this invention kills both lipophilic and hydrophilic viruses. Contrary to quaternary ammoniums, the formulation of this invention kills mycobacteria, hydrophilic viruses and wet bacterial spores.

The composition of this invention is also extremely efficient in spray form or at lower concentration as can be seen from the comparative laboratory results given in Table XI with phenol and chlorine. While the chlorine theoretically seems to present an advantage at concentrations below 0.02%, one must remember that in actual practice the presence of traces of organic matter will quickly inactivate the chlorine. This alone explains why higher hatchability gains are achieved with glutaraldehyde. In practice, the potentiated solutions of this invention show no decrease in activity in the presence of 20% protein (horse serum) while chlorine and phenol cidal efficiencies drop sharply in the presence of 1% of organic matter (1% peptone DIFCO in our tests).

The glutaraldehyde compositions of this invention exhibit the following important advantages:

They maintain their cidal activity (specially against vegetative organisms) at dilutions as low as 0.02%.

They can act upon a wider range of microorganisms than the phenol, chlorine and quaternary ammonium formulations.

They are extremely stable and can be used in the presence of heat or ultrasounds.

They can be reused over a period of several months without losing their potency.

They can provide a thorough cleaning (removal of soil or organic matters) while at the same time giving a high cidal efficiency.

In the Tables potentiated glutaraldehyde is glutaraldehyde, and the nonionic ethoxylates of isomeric linear alcohols. A 2% potentiated glutaraldehyde solution is 2% glutaraldehyde, 0.25% ethoxylates of isomeric linear alcohols and remainder water.

Although several specific examples of the inventive concept have been described for purposes of illustration, the invention should not be construed as limited thereby nor to the specific features mentioned therein except as the same may be included in the claims appended hereto. It is also understood that changes, modifications, and variations may be made without departing from the spirit and scope of the present invention.

The embodiments of the invention in which an exclusive property or privilege is claimed are defined in claims as follows.

TABLE VI

The effect of potentiated glutaraldehyde on hatchability of broiler eggs.
Laboratory Hatchability Tests with potentiated glutaraldehyde (2%)

Fertile broiler eggs were dipped in a 2% solution of Potentiated glutaraldehyde as follows:

| Contact Time (Min.) | Test Conditions | Hatched | Unhatched | Culls |
|---|---|---|---|---|
| 0.5 | Dipped | 23 | 1 | 1 |
| 2.0 | Dipped | 22 | 2 | 1 |
| 10.0 | Dipped | 24 | — | 2 |
| 0.5 | Washed, then dipped | 23 | 1 | 1 |
| 2.0 | Washed, then dipped | 22 | 1 | 6(1 PIP) |
| 10.0 | Washed, then dipped | 23 | 1 | 2 |
| 0.0 | Washed only control | 23 | 1 | 1 |
| 0.5 | Dipped, then rinsed | 22 | 2 | 1 |
| 2.0 | Dipped, then rinsed | 24 | 0 | 1 |

Average Hatchability of treated eggs: 95%
Control (plant): Average Hatchability: 87%

TABLE VII

Germicidal effect of potentiated glutaraldehyde on surfaces of broiler eggs.

| Contact Time (Min.) | Test Conditions | Plate Counts Total Count | Plate Counts Total Coliforms | Total Fecal Coliforms |
|---|---|---|---|---|
| 0.5 | Dipped | 0 | 0 | 0 |
| 2.0 | Dipped | 0 | 0 | 0 |
| 10.0 | Dipped | 0 | 0 | 0 |
| 0.0 | Control | 20 | 1 | 0 |
| 0.5 | Washed, then dipped | 0 | 0 | 0 |
| 2.0 | Washed, then dipped | 0 | 0 | 0 |
| 10.0 | Washed, then dipped | 0 | 0 | 0 |
| 0.0 | Washed only control | 12 | 0 | 0 |
| 0.5 | Dipped, then rinsed | 0 | 0 | 0 |
| 2.0 | Dipped, then rinsed | 0 | 0 | 0 |
| 10.0 | Dipped, then rinsed | 0 | 0 | 0 |
| 0.0 | Rinsed only control | 18 | 0 | 0 |

TABLE VIII

*SONACIDE Test (Hatchery Dip)

| Breeder Flock | Number of Eggs | Chicks | Percent Hatchability | Percent Increase in Hatchability |
|---|---|---|---|---|
| H-24 Dipped | 144 | 127 | 88.1% | 7% |
| H-24 Balance | 33,612 | 27,262 | 81.1 | |
| F-22 Dipped | 138 | 121 | 87.6 | 10.5 |
| F-22 Balance | 24,124 | 18,600 | 77.1 | |
| T-25 Dipped | 152 | 131 | 86.1 | 4.8 |
| T-25 Balance | 20,968 | 17,047 | 81.3 | |
| | | | Average | 7.4% |

* Registered Trademark for 2% Glutaraldehyde
0.025% ethoxylates of isomeric linear alcohols

TABLE IX

| | Dipping treatment with various types of eggs- Percentage of Hatchability | | | | |
|---|---|---|---|---|---|
| | Potentiated glutaraldehyde 2% solution treatment 30 seconds | | Control (No treatment) | | Hatchability gain in percent |
| Nest Clean Eggs | (47/60) | 78.3% | (22/30) | 73.3% | + 5% |
| Nest Dirty Eggs | (42/50) | 84.0% | (22/25) | 80. % | + 4% |
| Floor Eggs | (13/20) | 65% | (4/11) | 36.4% | +28.6% |

TABLE X

| | Dipping treatment with a potentiated * glutaraldehyde solution (1%) and one year old used solution. | | |
|---|---|---|---|
| | | Percentage of Normal Hatched Eggs | |
| | 1% fresh solution | 1% one year old used solution | Control |
| Nest Cleaned Eggs | 79% | 78% | 73.3% |
| Nest Dirty Eggs | 83 | 84.5 | 80 |
| Floor Eggs | 65.5 | 66 | 36.4 |

* 1% Glutaraldehyde
0.125% ethoxylates of isomeric linear alcohols

TABLE XI

Comparative study of the cidal efficacy
of Phenol, Chlorine and potentiated glutaraldehyde
CONTACT TIME: 20°C
INCUBATION TEMP: 37.0°C
TESTS CULTURE: S. aureus (ATCC No. 6538)

| CONCENTRATION ACTIVE INGREDIENT | | PHENOL | | | AVAILABLE CHLORINE | | | POTENTIATED GLUTARALDEHYDE* | | |
|---|---|---|---|---|---|---|---|---|---|---|
| (ppm) | percentage | 1 | 5 | 10 | 1 | 5 | 10 | 1 | 5 | 10(min.) |
| 50 | 0.005% | + | + | + | 0 | 0 | 0 | + | + | + |
| 100 | 0.01 | + | + | + | 0 | 0 | 0 | + | + | 0 |
| 200 | 0.02 | + | + | + | 0 | 0 | 0 | + | 0 | 0 |
| 400 | 0.04 | + | + | + | 0 | 0 | 0 | 0 | 0 | 0 |
| 600 | 0.06 | + | + | + | 0 | 0 | 0 | 0 | 0 | 0 |
| 800 | 0.08 | + | + | 0 | 0 | 0 | 0 | 0 | 0 | 0 |
| 1000 | 0.1 | + | 0 | 0 | 0 | 0 | 0 | 0 | 0 | 0 |

*2% glutaraldehyde plus 0.25% ethoxylates of isomeric linear alcohols.
This test is a variation of AOAC 4.004 where concentration of phenol are compared with disinfectants at varying times of contact, but using known levels of the disinfectant.

What is claimed is:

1. A method of disinfecting and sanitizing fowl eggs comprising contacting said eggs with a sufficient amount of a composition to disinfect and sanitize comprising from about 0.02% to about 5% of glutaraldehyde and from about 0.01% to 1% of a nonionic surface active agent which is an ethoxylate of isomeric linear alcohols having the following formula:

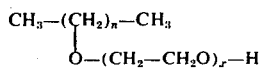

wherein $n$ is 9 to 13 and $x$ is 9 to 13.

2. The method of claim 1 wherein the composition contains at least one solvent selected from the group consisting of water and lower alcohol.

3. The method of claim 2 wherein the composition contains a sufficient quantity of a lower alkanol to make a final alcoholic concentration of from about 60% to about 75%.

4. The method of claim 1 wherein the eggs are contacted with the composition by dipping the eggs in the composition.

5. The method of claim 1 wherein the eggs are contacted with the composition by spraying the eggs with the composition.